(12) United States Patent
Weeber

(10) Patent No.: US 10,288,901 B2
(45) Date of Patent: May 14, 2019

(54) LIMITED ECHELLETTE LENS, SYSTEMS AND METHODS

(71) Applicant: AMO GRONINGEN B.V., Groningen (NL)

(72) Inventor: Hendrik A. Weeber, Groningen (NL)

(73) Assignee: AMO GRONINGEN B.V., Groningen (NL)

( * ) Notice: Subject to any disclaimer, the term of this patent is extended or adjusted under 35 U.S.C. 154(b) by 3 days.

(21) Appl. No.: 15/415,736

(22) Filed: Jan. 25, 2017

(65) Prior Publication Data

US 2017/0131565 A1 May 11, 2017

Related U.S. Application Data

(60) Continuation of application No. 14/472,815, filed on Aug. 29, 2014, now Pat. No. 9,557,580, which is a
(Continued)

(51) Int. Cl.
  *G02C 7/02* (2006.01)
  *G02C 7/04* (2006.01)
(Continued)

(52) U.S. Cl.
  CPC .............. *G02C 7/022* (2013.01); *A61B 34/10* (2016.02); *A61F 2/16* (2013.01); *A61F 2/164* (2015.04); *A61F 2/1613* (2013.01); *A61F 2/1618* (2013.01); *A61F 2/1645* (2015.04); *A61F 2/1654* (2013.01); *G02B 27/0075* (2013.01); *G02C 7/027* (2013.01); *G02C 7/041* (2013.01); *G02C 7/044* (2013.01); *G02C 7/049* (2013.01); *G02C 7/06* (2013.01); *A61B 2034/104* (2016.02); *A61F 2/1637* (2013.01); *A61F 2230/0006* (2013.01); *G02C 2202/20* (2013.01)

(58) Field of Classification Search
  CPC . G02C 7/02; G02C 7/022; G02C 7/04; G02C 7/041; G02C 7/042; G02C 7/043; G02C 7/044; G02C 7/045; G02C 7/049
  USPC ............. 351/159.01, 159.02, 159.11–159.13, 351/159.15, 159.26, 159.35, 159.44
  See application file for complete search history.

(56) References Cited

U.S. PATENT DOCUMENTS 2,077,092 A   4/1937  Broder
3,305,294 A   2/1967  Alvarez
(Continued)

FOREIGN PATENT DOCUMENTS

CA   2722274 A1   10/2009
CN   1035363 A    9/1989
(Continued)

OTHER PUBLICATIONS

Alfonso J.F., et al., "Prospective Study of the Acri.LISA Bifocal Intraocular Lens," Journal of Cataract Refractive Surgery, Nov. 2007, vol. 33 (11), pp. 1930-1935.
(Continued)

*Primary Examiner* — Darryl J Collins
(74) *Attorney, Agent, or Firm* — Johnson & Johnson Surgical Vision, Inc.

(57) ABSTRACT

An ophthalmic lens with a circular surface structure and limited adjacent echelettes that provides enhanced image quality across an extended range of foci.

33 Claims, 8 Drawing Sheets

Related U.S. Application Data continuation of application No. 13/934,556, filed on Jul. 3, 2013, now Pat. No. 8,820,927, which is a division of application No. 12/971,607, filed on Dec. 17, 2010, now Pat. No. 8,480,228.

(60) Provisional application No. 61/288,255, filed on Dec. 18, 2009.

(51) Int. Cl.
  *A61F 2/16* (2006.01)
  *G02C 7/06* (2006.01)
  *G02B 27/00* (2006.01)
  *A61B 34/10* (2016.01)

(56) References Cited

U.S. PATENT DOCUMENTS

| | | |
|---|---|---|
| 3,367,734 A | 2/1968 | Karl et al. |
| 3,735,685 A | 5/1973 | Plummer |
| 4,010,496 A | 3/1977 | Neefe |
| 4,077,071 A | 3/1978 | Freeman |
| 4,093,361 A | 6/1978 | Erickson et al. |
| 4,134,160 A | 1/1979 | Bayers |
| 4,162,122 A | 7/1979 | Cohen |
| 4,174,543 A | 11/1979 | Kelman |
| 4,210,391 A | 7/1980 | Cohen |
| 4,249,272 A | 2/1981 | Poler |
| 4,254,509 A | 3/1981 | Tennant |
| 4,254,510 A | 3/1981 | Tennant |
| 4,316,293 A | 2/1982 | Bayers |
| 4,319,564 A | 3/1982 | Karickhoff |
| 4,338,005 A | 7/1982 | Cohen |
| 4,340,283 A | 7/1982 | Cohen |
| 4,370,760 A | 2/1983 | Kelman |
| 4,377,873 A | 3/1983 | Reichert |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,593,981 A | 6/1986 | Scilipoti |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,636,049 A | 1/1987 | Blaker |
| 4,637,697 A | 1/1987 | Freeman |
| 4,642,112 A | 2/1987 | Freeman |
| 4,655,565 A | 4/1987 | Freeman |
| 4,673,406 A | 6/1987 | Schlegel |
| 4,676,791 A | 6/1987 | Lemaster et al. |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,734,095 A | 3/1988 | Siepser |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin et al. |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,539 A | 9/1989 | Lee et al. |
| 4,898,461 A | 2/1990 | Portney |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,184,405 A | 2/1993 | Cress |
| 5,197,981 A | 3/1993 | Southard |
| 5,201,763 A | 4/1993 | Brady et al. |
| 5,203,790 A | 4/1993 | McDonald |
| 5,217,491 A | 6/1993 | Vanderbilt |
| 5,225,858 A | 7/1993 | Portney |
| 5,225,997 A | 7/1993 | Lederer et al. |
| 5,229,797 A | 7/1993 | Futhey et al. |
| 5,258,025 A | 11/1993 | Fedorov et al. |
| 5,278,592 A | 1/1994 | Marie et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,567,365 A | 10/1996 | Weinschenk, III et al. |
| 5,571,177 A | 11/1996 | Deacon et al. |
| 5,620,720 A | 4/1997 | Glick et al. |
| 5,628,796 A | 5/1997 | Suzuki |
| 5,652,638 A | 7/1997 | Roffman et al. |
| 5,691,800 A | 11/1997 | Iki et al. |
| 5,699,142 A | 12/1997 | Lee et al. |
| 5,715,031 A | 2/1998 | Roffman et al. |
| 5,716,403 A | 2/1998 | Tran et al. |
| 5,748,282 A | 5/1998 | Freeman |
| 5,760,871 A | 6/1998 | Kosoburd et al. |
| 5,796,462 A | 8/1998 | Roffman et al. |
| 5,801,807 A | 9/1998 | Satake et al. |
| 5,928,282 A | 7/1999 | Nigam |
| 5,968,094 A | 10/1999 | Werblin et al. |
| 6,015,435 A | 1/2000 | Valunin et al. |
| 6,051,024 A | 4/2000 | Cumming |
| 6,055,111 A | 4/2000 | Nomura et al. |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,179,870 B1 | 1/2001 | Sourdille et al. |
| 6,210,005 B1 | 4/2001 | Portney |
| 6,235,055 B1 | 5/2001 | Chu |
| 6,261,321 B1 | 7/2001 | Kellan |
| 6,319,282 B1 | 11/2001 | Nishi |
| 6,338,559 B1 | 1/2002 | Williams et al. |
| 6,419,697 B1 | 7/2002 | Kelman |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |

(56) References Cited

U.S. PATENT DOCUMENTS

| | | |
|---|---|---|
| 6,557,992 B1 | 5/2003 | Dwyer et al. |
| 6,598,606 B2 | 7/2003 | Terwee et al. |
| 6,609,793 B2 | 8/2003 | Norrby et al. |
| 6,705,729 B2 | 3/2004 | Piers et al. |
| 6,709,102 B2 | 3/2004 | Duppstadt |
| 6,802,605 B2 | 10/2004 | Cox et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,615,073 B2 | 11/2009 | Deacon et al. |
| 7,616,330 B2 | 11/2009 | Neal et al. |
| 7,713,299 B2 | 5/2010 | Brady et al. |
| 7,794,497 B2 | 9/2010 | Brady et al. |
| 7,857,451 B2 | 12/2010 | Thibos et al. |
| 7,871,162 B2 | 1/2011 | Weeber |
| 7,993,398 B2 | 8/2011 | Deacon et al. |
| 8,002,827 B2 | 8/2011 | Deacon et al. |
| 8,018,164 B2 | 9/2011 | Shannon et al. |
| 8,231,219 B2 | 7/2012 | Weeber |
| 8,241,354 B2 | 8/2012 | Hong et al. |
| 8,382,281 B2 | 2/2013 | Weeber |
| 8,430,508 B2 | 4/2013 | Weeber |
| 8,480,228 B2 | 7/2013 | Weeber |
| 8,573,775 B2 | 11/2013 | Weeber |
| 8,747,466 B2 | 6/2014 | Weeber et al. |
| 8,770,745 B2 | 7/2014 | Lindacher et al. |
| 8,862,447 B2 | 10/2014 | Weeber |
| 9,335,563 B2 | 5/2016 | Weeber |
| 2001/0035935 A1 | 11/2001 | Bhalakia et al. |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0054358 A1 | 3/2004 | Cox |
| 2004/0068317 A1 | 4/2004 | Knight |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150790 A1 | 8/2004 | Roffman et al. |
| 2004/0156014 A1 | 8/2004 | Piers et al. |
| 2004/0167622 A1 | 8/2004 | Sunalp et al. |
| 2005/0096226 A1 | 5/2005 | Stock et al. |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0066808 A1 | 3/2006 | Blum et al. |
| 2006/0068453 A1 | 3/2006 | Altieri |
| 2006/0098162 A1* | 5/2006 | Bandhauer ............ A61F 2/1618 351/159.44 |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0238702 A1 | 10/2006 | Glick et al. |
| 2006/0244904 A1 | 11/2006 | Hong et al. |
| 2006/0244916 A1 | 11/2006 | Guillon |
| 2006/0279700 A1 | 12/2006 | Liang |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 | 11/2007 | Hong et al. |
| 2008/0018910 A1 | 1/2008 | Neal et al. |
| 2008/0030677 A1 | 2/2008 | Simpson |
| 2008/0161913 A1 | 7/2008 | Brady et al. |
| 2008/0161914 A1 | 7/2008 | Brady et al. |
| 2008/0231809 A1 | 9/2008 | Haigis |
| 2008/0269642 A1 | 10/2008 | Deacon et al. |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0051876 A1 | 2/2009 | Seiler et al. |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0187242 A1 | 7/2009 | Weeber et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0279048 A1 | 11/2009 | Hong et al. |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0016965 A1 | 1/2010 | Hong et al. |
| 2010/0082017 A1 | 4/2010 | Zickler et al. |
| 2010/0100178 A1 | 4/2010 | Weeber et al. |
| 2010/0130888 A1 | 5/2010 | Deacon et al. |
| 2010/0161048 A1 | 6/2010 | Schaper, Jr. |
| 2010/0274234 A1 | 10/2010 | Liang |
| 2012/0140166 A1 | 6/2012 | Zhao |
| 2012/0320334 A1 | 12/2012 | Ho et al. |

FOREIGN PATENT DOCUMENTS

| | | |
|---|---|---|
| CN | 1039487 A | 2/1990 |
| CN | 1406120 A | 3/2003 |
| CN | 1833192 A | 9/2006 |
| DE | 8107675 U1 | 7/1981 |
| DE | 3439551 A1 | 4/1986 |
| EP | 226400 A2 | 6/1987 |
| EP | 227357 A2 | 7/1987 |
| EP | 0343067 A1 | 11/1989 |
| EP | 0457553 A2 | 11/1991 |
| EP | 681198 A1 | 11/1995 |
| EP | 0926531 A1 | 6/1999 |
| EP | 949529 A2 | 10/1999 |
| EP | 957331 A2 | 11/1999 |
| EP | 1424049 A1 | 6/2004 |
| EP | 1310267 B1 | 1/2008 |
| EP | 1424049 B1 | 6/2009 |
| EP | 2182891 B1 | 4/2014 |
| FR | 2745711 A1 | 9/1997 |
| JP | H0255314 A | 2/1990 |
| WO | 8603961 A1 | 7/1986 |
| WO | 9222264 A1 | 12/1992 |
| WO | 9303409 A1 | 2/1993 |
| WO | 9507487 A1 | 3/1995 |
| WO | 9856315 A1 | 12/1998 |
| WO | 0019906 A1 | 4/2000 |
| WO | 0111418 A1 | 2/2001 |
| WO | 0135868 A1 | 5/2001 |
| WO | 0154569 A1 | 8/2001 |
| WO | 0163344 A1 | 8/2001 |
| WO | 0182839 A1 | 11/2001 |
| WO | 0189424 A1 | 11/2001 |

(56) References Cited

FOREIGN PATENT DOCUMENTS

| | | |
|---|---|---|
| WO | 0221194 A2 | 3/2002 |
| WO | 03009053 A1 | 1/2003 |
| WO | 2004034129 A1 | 4/2004 |
| WO | 04090611 A2 | 10/2004 |
| WO | 04096014 A2 | 11/2004 |
| WO | 05019906 A1 | 3/2005 |
| WO | 06025726 A1 | 3/2006 |
| WO | 2006032263 A2 | 3/2006 |
| WO | 06047698 A1 | 5/2006 |
| WO | 06060477 A2 | 6/2006 |
| WO | 06060480 A2 | 6/2006 |
| WO | 2007067872 A2 | 6/2007 |
| WO | 2007092948 A1 | 8/2007 |
| WO | 2007133384 A2 | 11/2007 |
| WO | 2008045847 A2 | 4/2008 |
| WO | 2008083283 A2 | 7/2008 |
| WO | 2009020963 A1 | 2/2009 |
| WO | 2009029515 A1 | 3/2009 |
| WO | 2009058755 A1 | 5/2009 |
| WO | 2009076670 A1 | 6/2009 |
| WO | 2009137491 A1 | 11/2009 |
| WO | 2010009254 A1 | 1/2010 |
| WO | 2010009257 A1 | 1/2010 |

OTHER PUBLICATIONS

Alio J.L., et al., "Phakic Anterior Chamber Lenses for the Correction of Myopia: A 7-Year Cumulative Analysis of Complications in 263 Cases," Ophthalmology, 1999, vol. 106 (3), pp. 458-466.
Apple D.J., et al., "Anterior Chamber Lenses Part 1: Complications and Pathology and a Review of Designs," Journal of Cataract Refractive Surgery, 1987, vol. 13 (2), pp. 157-174.
Apple D.J., et al., Eds., "Intraocular Lenses: Evolution, Designs, Complications and Pathology," in: New Concepts in Intraocular Lens Implantation, Williams & Wilkins publisher, 1989, vol. 36 (1), pp. 21-36.
Apple D.J., et al., Eds., "Intraocular Lenses: Evolution, Designs, Complications and Pathology," in: New Concepts in Intraocular Lens Implantation, Williams & Wilkins publisher, 1989, vol. 22 (36), pp. 205-221.
Baikoff G., et al., "Angle-fixated Anterior Chamber Phakic Intraocular Lens for Myopia 7 to -19 Diopters," Journal of Refractive Surgery, 1998, vol. 14 (3), pp. 282-292.
Canovas C., et al., "Hybrid Adaptive-Optics Visual Simulator," Optical Letters, Jan. 15, 2010, vol. 35 (2), pp. 196-198.
Cheng X., et al., "Predicting Subjective Judgment of Best Focus with Objective Image Quality Metrics," Journal of Vision, 2004, vol. 4 (4), pp. 310-321.
CILCO Advertisement Brochure, Oct. 1982, 3 pages.
Cohen A.L., "Practical Design of a Bifocal Hologram Contact Lens or Intraocular Lens," Applied Optics, Jul. 1, 1992, vol. 31 (19), pp. 3750-3754.
Co-pending U.S. Appl. No. 11/618,325, filed Dec. 29, 2006.
Co-pending U.S. Appl. No. 11/618,411, filed Dec. 29, 2006.
De Almeida M.S., et al., "Different Schematic Eyes and their Accuracy to the in Vivo Eye: A Quantitative Comparison Study," Brazilian Journal of Physics, 2007, vol. 37 (2A), 10 pages.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
European Search Report for Application No. EP11165087, dated Jul. 22, 2011, 6 pages.
European Search Report for Application No. EP89304883, dated Sep. 3, 1990, 1 page.
International Search Report and Written Opinion for Application No. PCT/IB2011/001067, dated Sep. 13, 2011, 13 pages.
International Search Report and Written opinion for Application No. PCT/US08/061180, dated Sep. 5, 2008, 10 pages.
International Search Report and Written opinion for Application No. PCT/US09/038469, dated Aug. 10, 2009, 12 pages.
International Search Report and Written Opinion for Application No. PCT/US2011/026193, dated Jun. 7, 2011, 17 pages.
International Search Report for Application No. PCT/EP2008/061235, dated Mar. 5, 2009, 2 pages.
International Search Report for Application No. PCT/EP2009/051783, dated Apr. 28, 2009, 4 pages.
International Search Report for Application No. PCT/IB2009/005590, dated Sep. 30, 2009, 3 pages.
International Search Report for Application No. PCT/US08/073999, dated Dec. 3, 2008, 3 pages.
International Search Report for Application No. PCT/US09/042449, dated Nov. 5, 2009, 5 pages.
International Search Report for Application No. PCT/US2009/034555, dated May 18, 2009, 6 pages.
International Search Report for Application No. PCT/US2010/038167, dated Sep. 27, 2010, 2 pages.
International Search Report for Application No. PCT/US2010/061017, dated Jun. 16, 2011, 7 pages.
International Search Report for Application No. PCT/US2010/061042, dated Mar. 31, 2011, 3 pages.
International Search Report for Application No. PCT/US2010/061081, dated Jun. 6, 2011, 7 pages.
International Search Report for Application No. PCT/US2011/043119, dated Feb. 15, 2012, 6 pages.
Kim J.H., et al., "The Analysis of Predicted Capsular Bag Diameter using Modified Model of Capsule Measuring Ring in Asians," Clinical and Experimental Ophthalmology, 2008, vol. 36 (3), pp. 238-244.
Liou H.L., et al., "Anatomically Accurate, Finite Model Eye for Optical Modeling," Journal of Optical Society of America, Aug. 1997, vol. 14 (8), pp. 1684-1695.
Liou H.L., et al., "The Prediction of Spherical Aberration with Schematic Eyes," Ophthalmic and Physiological Optics, Jan. 1996, vol. 16 (4), pp. 348-354.
Marinho A., "Results are Encouraging for Phakic IOLs, but More Work is needed," Refractive Surgery, 2000, p. 12, 15.
Marsack J.D., et al., "Metrics of Optical Quality Derived from Wave Aberrations Predict Visual Performance," Journal of Vision, Apr. 2004, vol. 4 (4), pp. 322-328.
Menapace R., "The Capsular Tension Rings," Journal of Cataract & Refractive Surgery, 2008, Chap. 3, pp. 27-44.
Monsoriu J.A., et al., "Devil's Lenses," Optics Express, Oct. 17, 2007, vol. 15 (21), pp. 13858-13864.
Navarro R., et al., "Accommodation-Dependent Model of the Human Eye with Aspherics," Journal of the Optical Society of America, 1985, vol. 2 (8), pp. 1273-1281.
Nio Y.K., et al., "Effect of Intraocular Lens Implantation on Visual Acuity, Contrast Sensitivity, and Depth of Focus," Journal of Cataract and Refractive Surgery, 2003, vol. 29 (11), pp. 2073-2081.
Norrby S., et al., "Model Eyes for Evaluation of Intraocular Lenses," Applied Optics, Sep. 7, 2007, vol. 46 (26), pp. 6595-6605.
Olsen T., "Simple Method to Calculate the Surgically Induced Refractive Change," Journal of Cataract & Refractive Surgery, 1993, vol. 19 (2), pp. 319-320.
Piers P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.
Praeger D.L., "Praeger Technique for the Insertion of the Copeland Radial IOL Posterior Chamber Placement," Copeland Lens, 1982, 7 pages.
Siedlecki D., et al., "Radial Gradient index Intraocular Lens: a Theoretical Model," Journal of Modern Optics, Feb. 20-Mar. 10, 2008, vol. 55 (4-5), pp. 639-647.
Strenn K., et al., "Capsular bag Shrinkage after Implantation of an Open-Loop Silicone Lens and a Poly(methyl methacrylate) Capsule Tension Ring," Journal of Cataract and Refractive Surgery, 1997, vol. 23 (10), pp. 1543-1547.

(56) References Cited

OTHER PUBLICATIONS

Tehrani M., et al., "Capsule Measuring Ring to Predict Capsular Bag Diameter and Follow its Course after Foldable Intraocular Lens Implantation," Journal of Cataract Refractive Surgery, 2003, vol. 29 (11), pp. 2127-2134.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Van Den Berg T.J., "Analysis of Intraocular Straylight, Especially in Relation to Age," Optometry and Vision Science, Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Vass C., et al., "Prediction of Pseudophakic Capsular bag Diameter based on Biometric Variables," Journal of Cataract and Refractive Surgery, 1999, vol. 25 (10), pp. 1376-1381.

Villegas E.A., et al., "Correlation between Optical and Psychophy, Sical Parameters as a Function of Defocus," Optometry and Vision Science, Jan. 1, 2002, vol. 79 (1), pp. 60-67.

Venter, J.A., et al., "Visual Outcomes and Patient Satisfaction with a Rotational Asymmetric Refractive Intraocular Lens for Emmetropic Presbyopia," Cataract & Refractive Surgery, Mar. 2015, vol. 41 (3), pp. 585-593.

\* cited by examiner

LIMITED ECHELLETTE LENS, SYSTEMS AND METHODS

CROSS-REFERENCES TO RELATED APPLICATIONS

This application is a continuation of and claims priority to U.S. patent application Ser. No. 14/472,815, filed Aug. 29, 2014, which claims priority to U.S. patent application Ser. No. 13/934,556, filed on Jul. 3, 2013, now U.S. Pat. No. 8,820,927 which issued on Sep. 2, 2014, which claims priority to U.S. patent application Ser. No. 12/971,607, filed on Dec. 17, 2010, now U.S. Pat. No. 8,480,228 which issued on Jul. 9, 2013, which claims priority under 35 U.S.C § 119(e) to provisional application No. 61/288,255 filed on Dec. 18, 2009, the entire contents of all of which are incorporated herein by reference. This application is related to the following applications which were filed concurrently herewith: Single Microstructure Lens, Systems And Methods, U.S. patent application Ser. No. 12/971,506, filed on Dec. 17, 2010; Ophthalmic Lens, Systems And Methods With Angular Varying Phase Delay, U.S. patent application Ser. No. 12/971,889, filed on Dec. 17, 2010; and Ophthalmic Lens, Systems And Methods Having At Least One Rotationally Asymmetric Diffractive Structure, U.S. patent application Ser. No. 61/424,433, filed on Dec. 17, 2010. The entire contents of these three applications are also incorporated herein by reference. This application is also related to the following U.S. Patent Application Nos. 61/047,699 and Ser. No. 12/109,251, both filed on Apr. 24, 2008; Ser. No. 12/429,155 filed on Apr. 23, 2009; Ser. No. 12/372,573 filed on Feb. 17, 2009; Ser. No. 12/197,249 filed on Aug. 23, 2008; Ser. No. 12/120,201 filed on Apr. 13, 2008, and Ser. No. 12/771,550 filed on Apr. 30, 2010.

BACKGROUND OF THE INVENTION

Embodiments of the present invention relate to vision treatment techniques and in particular, to ophthalmic lenses such as, for example, contact lenses, corneal inlays or onlays, or intraocular lenses (IOLs) including, for example, phakic IOLs and piggyback IOLs (i.e. IOLs implanted in an eye already having an IOL).

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages, and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL".

Monofocal IOLs are intended to provide vision correction at one distance only, usually the far focus. Predicting the most appropriate IOL power for implantation has limited accuracy, and an inappropriate IOL power can leave patients with residual refraction following surgery. Accordingly, it may be necessary for a patient who has received an IOL implant to also wear spectacles to achieve good far vision. At the very least, since a monofocal IOL provides vision treatment at only one distance and since the typical correction is for far distance, spectacles are usually needed for good near vision and sometimes intermediate vision. The term "near vision" generally corresponds to vision provided when objects are at a distance from the subject eye of between about 1 to 2 feet are substantially in focus on the retina of the eye. The term "distant vision" generally corresponds to vision provided when objects at a distance of at least about 6 feet or greater are substantially in focus on the retina of the eye. The term "intermediate vision" corresponds to vision provided when objects at a distance of about 2 feet to about 5 feet from the subject eye are substantially in focus on the retina of the eye.

There have been various attempts to address limitations associated with monofocal IOLs. For example, multifocal IOLs have been proposed that deliver, in principle, two foci, one near and one far, optionally with some degree of intermediate focus. Such multifocal or bifocal IOLs are intended to provide good vision at two distances, and include both refractive and diffractive multifocal IOLs. In some instances, a multifocal IOL intended to correct vision at two distances may provide a near add power of about 3.5 or 4.0 diopters.

Multifocal IOLs may, for example, rely on a diffractive optical surface to direct portions of the light energy toward differing focal distances, thereby allowing the patient to clearly see both near and far objects. Multifocal ophthalmic lenses (including contact lenses or the like) have also been proposed for treatment of presbyopia without removal of the natural crystalline lens. Diffractive optical surfaces, either monofocal or multifocal, may also be configured to provide reduced chromatic aberration.

Diffractive monofocal and multifocal lenses can make use of a material having a given refractive index and a surface curvature which provide a refractive power. Diffractive lenses have a diffractive profile which confers the lens with a diffractive power that contributes to the overall optical power of the lens. The diffractive profile is typically characterized by a number of diffractive zones. When used for ophthalmic lenses these zones are typically annular lens zones, or echelettes, spaced about the optical axis of the lens. Each echelette may be defined by an optical zone, a transition zone between the optical zone and an optical zone of an adjacent echelette, and an echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different add powers. Together, these echelettes form a diffractive profile.

A multifocal diffractive profile of the lens may be used to mitigate presbyopia by providing two or more optical powers; for example, one for near vision and one for far vision. The lenses may also take the form of an intraocular lens placed within the capsular bag of the eye, replacing the original lens, or placed in front of the natural crystalline lens.

The lenses may be in the form of a contact lens, most commonly a bifocal contact lens, or in any other form mentioned herein.

Although multifocal ophthalmic lenses lead to improved quality of vision for many patients, additional improvements would be beneficial. For example, some pseudophakic patients experience undesirable visual effects (dysphotopsia), e.g. glare or halos. Halos may arise when light from the unused focal image creates an out-of-focus image that is superimposed on the used focal image. For example, if light from a distant point source is imaged onto the retina by the distant focus of a bifocal IOL, the near focus of the IOL will simultaneously superimpose a defocused image on top of the image formed by the distant focus. This defocused image may manifest itself in the form of a ring of light surrounding the in-focus image, and is referred to as a halo. Another area of improvement revolves around the typical bifocality of multifocal lenses. Since multifocal ophthalmic lenses typically provide for near and far vision, intermediate vision may be compromised.

A lens with an extended depth of focus may provide certain patients the benefits of good vision at a range of distances, while having reduced or no dysphotopsia. Various techniques for extending the depth of focus of an IOL have been proposed. For example, some approaches are based on a bulls-eye refractive principle, and involve a central zone with a slightly increased power. Other techniques include an asphere or include refractive zones with different refractive zonal powers.

Although certain proposed treatments may provide some benefit to patients in need thereof, still further advances would be desirable. For example, it would be desirable to provide improved IOL systems and methods that confer enhanced image quality across a wide and extended range of foci without dysphotopsia. Embodiments of the present invention provide solutions that address the problems described above, and hence provide answers to at least some of these outstanding needs.

BRIEF SUMMARY OF THE INVENTION

Embodiments of the present invention generally provide improved lenses and imaging techniques. Exemplary embodiments provide improved ophthalmic lenses (such as, for example, contact lenses, corneal inlays or onlays, or intraocular lenses (IOLs) including, for example, phakic IOLs and piggyback IOLs) and associated methods for their design and use.

Embodiments of the present invention encompass IOL optics having a circular surface structure with one to four echelettes surrounding the surface structure. The profile is designed such that it increases the depth of focus of the pseudophakic eye, where the natural crystalline lens of the eye is substituted with a synthetic lens. Such limited ring IOL techniques suppress the distinct bifocality associated with traditional multifocal IOLs which have many diffractive rings. Consequently, dysphotopsia (e.g., halo effects) associated with traditional multifocal IOLs can be alleviated by lenses according to embodiments of the present invention.

An exemplary limited ring IOL includes an anterior face and a posterior face. A profile can be imposed on the anterior or posterior surface or face. The profile can have an inner portion and an outer portion. The inner portion typically presents a parabolic curved shape. The inner portion may also be referred to as a microstructure, or a central or inner echelette. Between the inner portion and the outer portion, there may be a transition zone that connects the inner and outer portions. The outer portion may be comprised of four or fewer echelettes.

In addition to parabolic shapes, the central/inner echelette can have any of a variety of shapes including hyperbolic, spherical, aspheric, and sinusoidal. The transition between the inner and outer portions of the central/inner echelette can be a sharp transition, or it can be a smooth transition.

The surface of the outer portion at the outside of the microstructure can have any spherical or aspherical shape and is comprised of a limited number of echelettes, preferably less than four. The shape of the outer portion can be optimized for having the desired optical performance for a range of pupil sizes. The desired optical performance can be based on elements such as the depth of focus, the optical quality in the far focus, and the change in best focus (or far focus) position as a function of the pupil size. Optimization rules may be applied as if the shape were a refractive monofocal IOL, or a refractive IOL having an extended depth of focus, or a refractive design that corrects or modifies the ocular spherical aberration. Specific designs can be made in which the interplay between the central echelette and the outer zone is incorporated in the design or optimization. The techniques described herein are well suited for implementation with any of a variety of ophthalmic lenses, including IOLs, corneal inlays or onlays, and/or contact lenses.

In one aspect, embodiments of the present invention encompass ophthalmic lens systems and methods for treating an eye of a patient. An exemplary lens may include an anterior face with an anterior refractive profile and a posterior face with a posterior refractive profile. The faces may be disposed about an optical axis. The lens may also include a diffractive profile imposed on the anterior refractive profile or the posterior refractive profile. In some cases, the diffractive profile may include no more than 5 echelettes. Optionally, the central echelette can be disposed within a central zone of the lens. Relatedly, the central echelette may be disposed within an annular ring surrounding a central refractive zone of the lens. In some cases, the lens includes a peripheral zone with a limited number of echelettes that surround the central echelette or annular ring. The limited number of echelettes may be characterized by a constant phase shift.

According to some embodiments, an ophthalmic lens can include a limited number of echelettes that are characterized by parabolic curves. The central echelette can have a diameter within a range from about 1 mm to about 4 mm. For example, the central echelette may have a diameter of about 1.5 mm. In some cases, the central echelette can have a diameter within a range from about 1.0 mm to about 5.0 mm. Lens embodiments may include a peripheral portion comprised of a limited number of echelettes and a refractive portion. Central and peripheral echelettes can have a surface area that is between 1 and 7 mm². For example, the echelettes may have a surface area that is 2.3 mm². In some cases, a lens may include a peripheral portion which surrounds the echelettes. A lens may include a peripheral portion having an outer diameter within a range from about 4 mm to about 6 mm. In some cases, the peripheral portion will have an outer diameter within a range of about 1 mm to about 7 mm. For example, a lens may include a peripheral portion having an outer diameter of about 5 mm.

The echelettes may be characterized by a step height having a value within a range from about 0.5 μm and about 4 μm. According to some embodiments, a transition can be characterized by a step height having a value within a range of about 1.5 μm and 2.5 μm. According to some embodiments, a transition can be characterized by a step height having a value of about 1.7 μm. In other embodiments, the step height may have a value of about 2.0 μm.

Optionally, a diffractive profile can be characterized by a design wavelength, and a lens can include a transition characterized by a step height producing a phase shift between about 0.25 and about 1 times the design wavelength. In some cases, a diffractive profile can be characterized by a design wavelength, and the lens can include a transition characterized by a step height producing a phase shift between about 0.15 and about 2 times the design wavelength.

In some aspects, embodiments of the present invention encompass systems and methods involving an ophthalmic lens that include an anterior face with an anterior refractive profile and a posterior face with a posterior refractive profile, such that the faces are disposed about an optical axis, and a diffractive profile imposed on the anterior refractive profile or the posterior refractive profile, such that the diffractive profile includes an inner echelette and four or fewer outer echelettes. According to some embodiments, an inner echelette can be disposed within a central zone of the lens. In some cases, an inner echelette can be disposed within an annular ring surrounding a central zone of the lens. Optionally, an inner echelette and outer echelettes can be characterized by a parabolic curve. In some cases, an inner echelette and outer echelettes can be characterized by a constant phase shift. According to some embodiments, an ophthalmic lens may include an accommodating lens and/or a multifocal lens.

For a fuller understanding of the nature and advantages of the present invention, reference should be had to the ensuing detailed description taken in conjunction with the accompanying drawings.

Figure 1A:
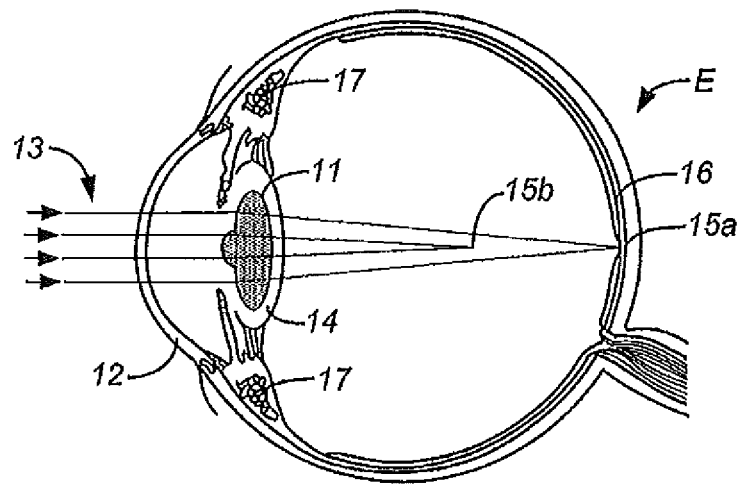
FIG. 1A is a cross-sectional view of an eye with a multifocal refractive intraocular lens.

For illustration purposes, the profile geometries shown in certain aforementioned figures were not drawn exactly to scale. The heights of the profiles shown in the figures are generally on the order of about 0.1 μm to about 8.0 μm although the heights may vary depending on factors such as the amount of correction needed by the patient, the refractive index of the lens material and surrounding medium, and the desired distribution of light between wanted diffraction orders.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity and brevity, many other elements found in typical ophthalmic lenses, implantable optic apparatuses, systems and methods. Those of ordinary skill in the art may thus recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Embodiments of the present invention encompass systems and methods that provide improved image quality over an extended range of focal points or foci. Systems and methods disclosed herein can encompass various ophthalmic lenses such as, for example, contact lenses, intraocular lenses, spectacle lenses, and corneal inlays or onlays. Exemplary embodiments include ophthalmic lenses having an extended depth of focus, as compared to conventional monofocal lenses, and reduced dysphtopsia as compared to conventional multifocal ophthalmic lenses. In some cases, such techniques involve an IOL approach that includes a limited number of rings or echelettes, and typically involves an expanded depth of focus. Advantageously, such approaches can provide a patient with good distance vision, as well as good vision at intermediate distances without dysphotopsia.

Embodiments of the present invention generally provide improved lenses and imaging systems and may be incorporated into any system in which a lens with an extended depth of focus may be advantageous, such as camera/video lenses, including those used for surveillance or for surgical procedures, as well as for cameras in mobile phones or other related devices. Embodiments of the invention may find their most immediate use in the form of improved ophthalmic devices, systems, and methods. Exemplary embodiments of the present invention provide improved ophthalmic lenses (including, for example contact lenses, intraocular lenses (IOLs), corneal implants and the like) and associated methods for their design and use. Embodiments of the present invention may be used with monofocal diffractive or refractive lenses, bifocal diffractive or refractive lenses, and multifocal diffractive or refractive lenses, e.g. embodiments of the present invention could be added to the opposite surface of multifocal IOLs, e.g. TECNIS Multifocal or REZOOM or RESTOR IOLs. In other words, an extended depth of focus feature may be added to, for example the opposite surface of a diffractive or refractive multifocal embodiment.

In addition, an extended depth of focus feature may be added to, for example, a toric IOL, an IOL that modifies ocular spherical and/or chromatic aberration, and/or an accommodating IOL. In general, an extended depth of focus feature may be added to an IOL that modifies ocular aberrations.

Reading is often done in bright light conditions in which the pupil is small. In contrast, night-time driving is done in low light conditions in which the pupil is large. Embodiments of the present invention encompass lenses that relatively emphasize intermediate or near vision for small pupil sizes, while also relatively emphasizing far vision for large pupil sizes. In some such ophthalmic lenses, a greater proportion of light energy may be transmitted to the far focus from a peripheral portion of the lens to accommodate for low light, far viewing conditions such as night time driving, with the near or intermediate viewing receiving relatively more light energy from a central portion of the diffractive profile—for reading or computer work for example and/or to provide depth of focus and intermediate or near viewing under low light reading conditions as in for example reading restaurant menus.

FIG. 1A is a cross-sectional view of an eye E fit with a multifocal IOL 11. As shown, multifocal IOL 11 may, for example, comprise a bifocal IOL. Multifocal IOL 11 receives light from at least a portion of cornea 12 at the front of eye E and is generally centered about the optical axis of eye E. For ease of reference and clarity, FIGS. 1A and 1B do not disclose the refractive properties of other parts of the eye, such as the corneal surfaces. Only the refractive and/or diffractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens.

In a young, healthy eye contraction and relaxation of ciliary muscles 17 surrounding the capsular bag 14 contribute to accommodation of the eye, the process by which the eye increases optical power to maintain focus on objects as they move closer. As a person ages, the degree of accommodation decreases and presbyopia, the diminished ability to focus on near objects, often results. A patient may therefore conventionally use corrective optics having two optical powers, one for near vision and one for far vision, as provided by multifocal IOL 11.

Multifocal lenses may optionally also make special use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a higher surface curvature and a generally higher overall power (sometimes referred to as a positive add power) suitable for viewing at near distances.

Figure 1B:
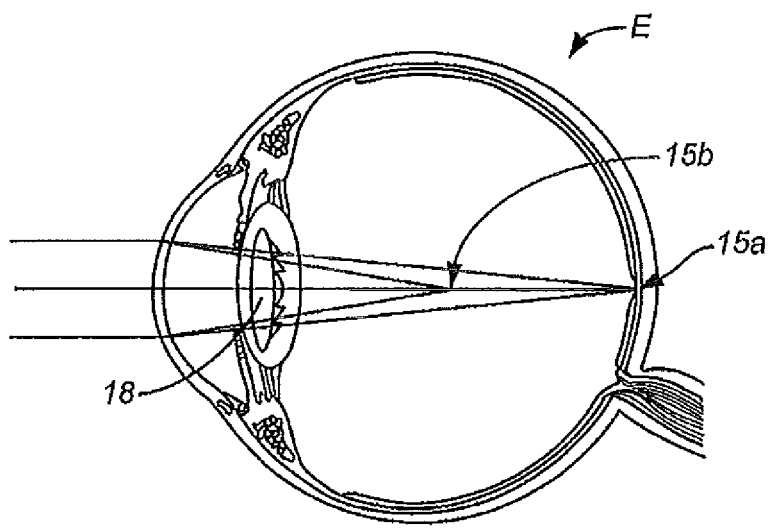
FIG. 1B is a cross-sectional view of an eye having an implanted multifocal diffractive intraocular lens.

Rather than relying entirely on the refractive properties of the lens, multifocal diffractive IOLs or contact lenses can also have a diffractive power, as illustrated by the IOL 18 shown in FIG. 1B. The diffractive power can, for example, comprise positive or negative add power, and that add power may be a significant (or even the primary) contributor to the overall optical power of the lens. The diffractive power is conferred by a plurality of concentric diffractive zones which form a diffractive profile. The diffractive profile may either be imposed on the anterior face or posterior face or both.

The diffractive profile of a diffractive multifocal lens directs incoming light into a number of diffraction orders. As light 13 enters from the front of the eye, the multifocal lens 18 directs light 13 to form a far field focus 15a on retina 16 for viewing distant objects and a near field focus 15b for viewing objects close to the eye. Depending on the distance from the source of light 13, the focus on retina 16 may be the near field focus 15b instead. Typically, far field focus 15a is associated with $0^{th}$ diffractive order and near field focus 15b is associated with the $1^{st}$ diffractive order, although other orders may be used as well.

Multifocal ophthalmic lens 18 typically distributes the majority of light energy into the two viewing orders, often with the goal of splitting imaging light energy about evenly (50%:50%), one viewing order corresponding to far vision and one viewing order corresponding to near vision, although typically, some fraction goes to non-viewing orders.

In some embodiments, corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present invention may be applied to inlays, onlays, accommodating IOLs, spectacles, and even laser vision correction.

Figure 2A:
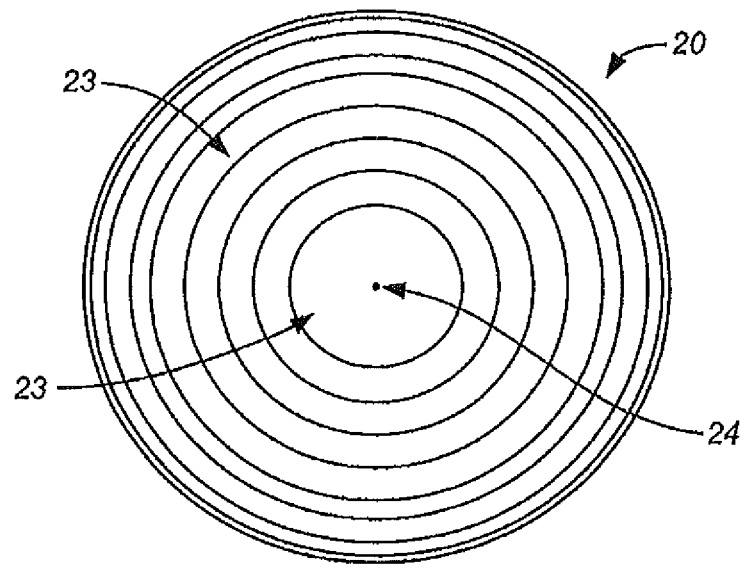
FIG. 2A is a front view of a diffractive multifocal ophthalmic lens.
Figure 2B:
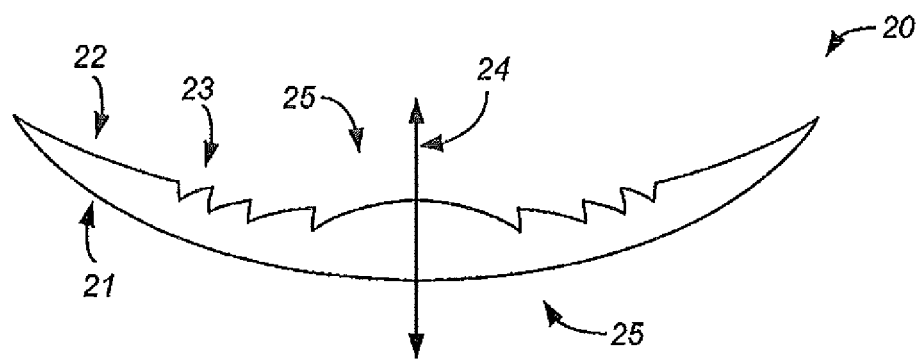
FIG. 2B is a cross-sectional view of the lens of FIG. 2A.

FIGS. 2A and 2B show aspects of a standard diffractive multifocal lens 20. Multifocal lens 20 may have certain optical properties that are generally similar to those of multifocal IOLs 11, 18 described above. Multifocal lens 20 has an anterior lens face 21 and a posterior lens face 22 disposed about optical axis 24. The faces 21, 22 of lens 20 typically define a clear aperture 25. As used herein, the term "clear aperture" means the opening of a lens or optic that restricts the extent of a bundle of light rays from a distant source that can be imaged or focused by the lens or optic. The clear aperture is usually circular and is specified by its diameter, and is sometimes equal to the full diameter of the optic.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be imposed on either anterior face 21 and posterior face 22 or both, FIG. 2B shows posterior face 22 with a diffractive profile. The diffractive profile is characterized by a plurality of annular optical zones or echelettes 23 spaced about optical axis 24. While analytical optics theory generally assumes an infinite number of echelettes, a standard multifocal diffractive IOL typically has at least 9 echelettes, and may have over 30 echelettes. For the sake of clarity, FIG. 2B shows only 4 echelettes. Typically, an IOL is biconvex, or possibly plano-convex, or convex-concave, although an IOL could be plano-plano, or other refractive surface combinations.

Figure 3A:
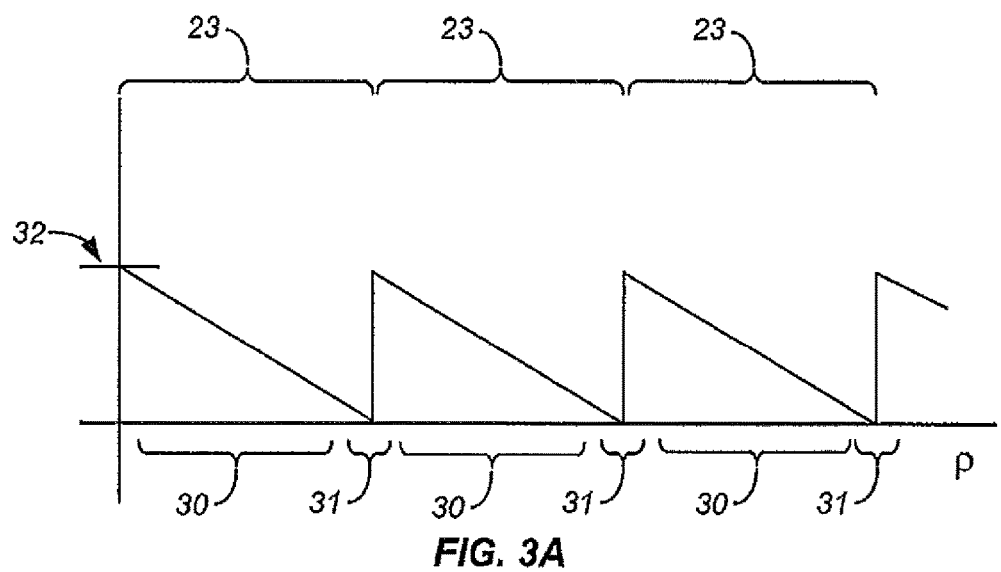
FIGS. 3A-3B are a graphical representations of a portion of the diffractive profile of a conventional diffractive multifocal lens.
Figure 3B:
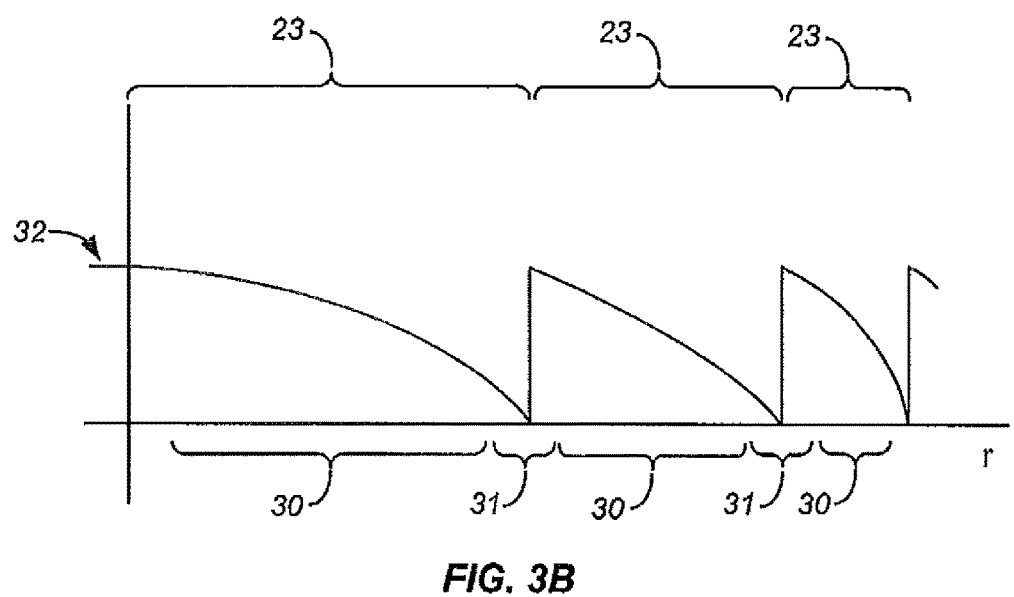

FIGS. 3A and 3B are graphical representations of a portion of a typical diffractive profile of a multifocal lens. While the graph shows only 3 full echelettes, typical diffractive lenses extend to at least 9 echelettes to over 32 echelettes. In FIG. 3A, the height of the surface relief profile (from a plane perpendicular to the light rays) of each point on the echelette surface is plotted against the square of the radial distance ($r^2$ or $\rho$) from the optical axis of the lens. In multifocal lenses, each echelette 23 may have a diameter or distance from the optical axis which is often proportional to $\sqrt{n}$, n being the number of the echelette 23 as counted from optical axis 24. Each echelette has a characteristic optical zone 30 and transition zone 31. Optical zone 30 has a shape or downward slope that may be linear when plotted against $\rho$ as shown in FIG. 3A. When plotted against radius r, optical zone 30 has a shape or downward slope that is parabolic as shown in FIG. 3B. As for the typical diffractive multifocal lens, as shown here, all echelettes have the same surface area. The area of echelettes 23 determines the add power of lens 20, and, as area and radii are correlated, the add power is also related to the radii of the echelettes.

As shown in FIGS. 3A and 3B, transition zone 31 between adjacent echelettes is sharp and discontinuous. The height of the lens face sharply transitions from sloping steadily downwards to stepping vertically upwards, and the transitions abruptly back to sloping steadily downwards again. In doing so, echelettes 23 also have a characteristic step height 32 defined by the distance between the lowest point and height point of the echelette. Hence, the slope (or first derivative) and/or the curvature (second derivative) of the diffractive surface are discontinuous adjacent the transitions.

Structure of Central Echelette

Figure 4:
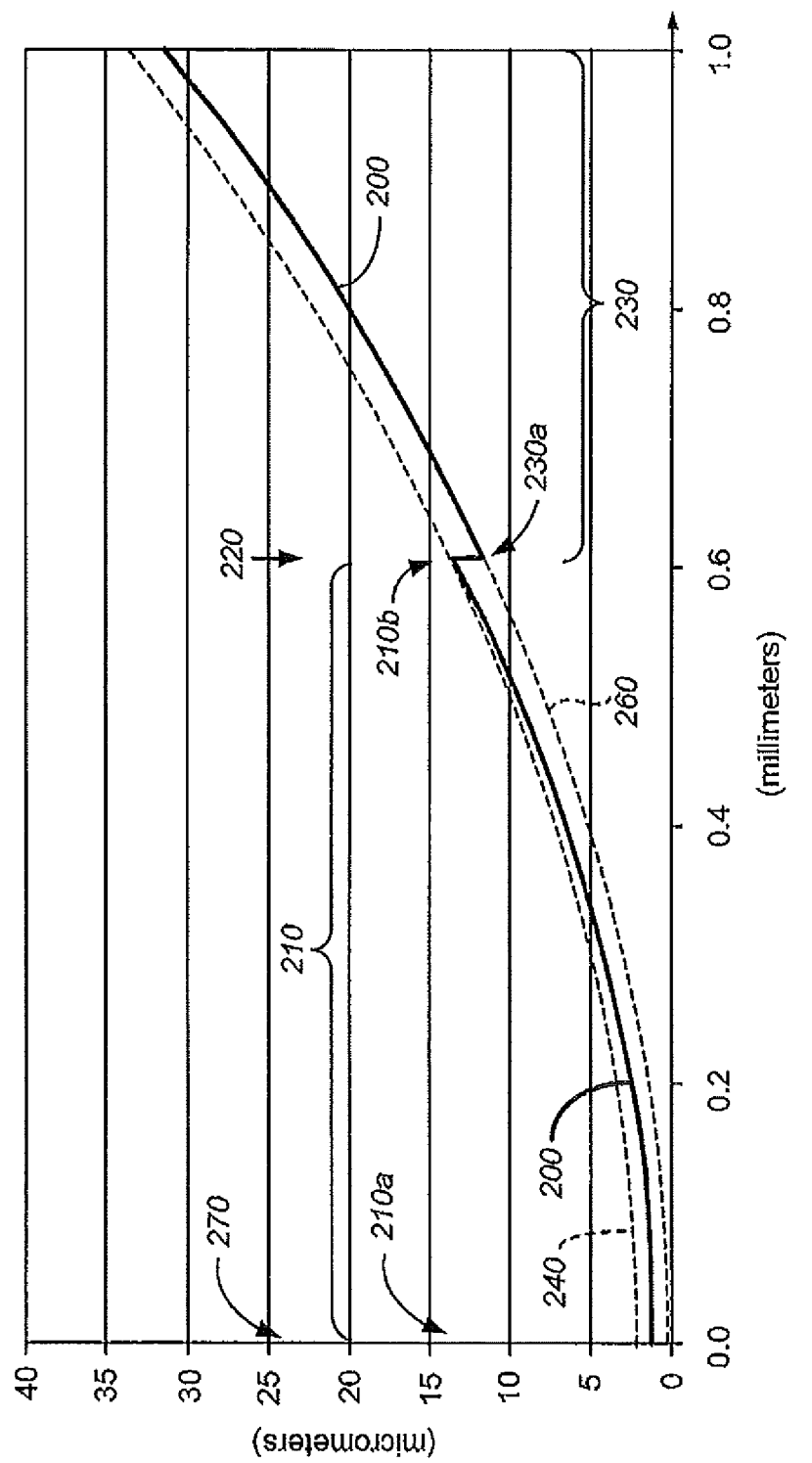
FIG. 4 shows aspects of the central echelette of a lens according to embodiments of the present invention.

FIG. 4 provides a graphical representation of a cross section of a portion of an exemplary lens illustrating the central echelette structure. The lens profile 200 has a ring diameter of 1.21 mm and a stepheight at 220 of 2.05 µm, corresponding with a phase delay of 0.5 lambda (see table 2). In this example, the ring diameter was reduced from 1.5 mm (which is the inner ring diameter for a 2.0 Diopter conventional IOL diffractive lens) to 1.21 mm by a scaling factor √2, as described in patent U.S. Pat. No. 5,121,980 (Cohen). Only the inner portion and part of the outer portion of half of the lens is shown, although since the lens is rotationally symmetric, the other half is a mirror image.

The adjacent echelette(s) in the outer portion (not shown) are detailed below. Profile 200 includes an inner portion 210 or single ring, a step or transition 220, and an outer portion 230. The outer portion 230 extends beyond that disclosed in FIG. 4F to 2.5 mm and may be comprised of limited additional echelettes. Inner portion 210 extends between a central location 210 of profile 200 and transition 220. Outer portion 230 extends between transition 220 and a peripheral location (not shown). In some cases, transition 220 can be disposed at a distance from the optical axis that is within a range from about 0.5 mm to about 2.0 mm, and peripheral location can be disposed at a distance from the optical axis that is within a range from about 2.0 to about 3.5 mm, or bigger (for example, for contact lenses, the ranges would be approximately 15% larger due to the optically more powerful position of contact lens compared to an IOL; those skilled in the art would appropriately scale certain dimensions depending on the application).

The inner portion or echelette 210 includes a center 210a and a peripheral edge 210b. At center or central section 210a of inner portion 210 where radial distance is zero, the sag (d) of inner portion is between the sag (d) of the diffractive base curve 240 and the sag (d) of the peripheral curve 260 at 1.03 µm from the peripheral curve 260, corresponding with a phase delay of 0.25 lambda (see table 2). At peripheral edge 210b, the sag (d) of inner portion 210 is substantially equivalent to the sag (d) of diffractive base curve 240 at 13.8 µm. The value of sag (d) between radial distance zero and radial distance at the peripheral edge 210b at 0.61 mm, gradually and smoothly changes from 1.03 µm (at r=0) to the value of the base curve 240 (at r=0.61 mm) which is 13.8 µm. This change occurs in a parabolic fashion. As shown here, inner portion can present a parabolic shape, for example as described in Equation 4a of Cohen, Applied Optics, 31:19, pp. 3750-3754 (1992), incorporated herein by reference.

At the peripheral edge 210b where the radial distance (r) is 0.61 mm, the value of sag (d) steps or changes from the value of diffractive base curve 240 to the value of peripheral curve 260. Where radial distance (r) corresponds to transition 220, sag (d) of inner portion is equivalent to the value of the diffractive base curve 240. Relatedly, the displacement of the profile approaches that of the diffractive base curve as the radial distance increases from a value of zero to a value of about 0.61 mm. The stepheight is 2.05 µm resulting in a phase delay of 0.5.

The outer portion 230 includes an inner or central edge 230a and a peripheral edge (not shown). At inner edge 230a, the sag (d) of outer portion is substantially equivalent to the sag (d) of peripheral curve 260. At peripheral edge, the sag (d) of outer portion remains substantially equivalent to the sag (d) of peripheral curve 260. As detailed below, a limited number of echelettes may be located between inner edge 230a and peripheral edge.

Figure 4A:
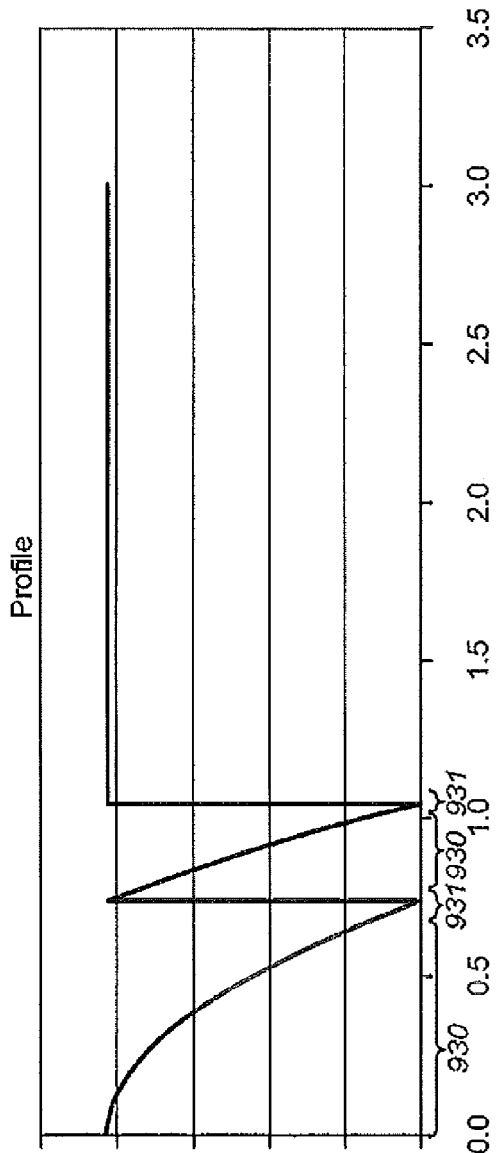
FIGS. 4A-4E illustrate aspects of a lens profile according to embodiments of the present invention.

FIG. 4A provides a graphical representation of a portion of a lens diffractive profile with a central echelette and one peripheral adjacent echelette according to embodiments of the present invention. In FIG. 4A, the height of the surface relief profile (from a plane perpendicular to the light rays) of each point on the echelettes surface is plotted against the distance from the optical axis of the lens. The echelettes can have a characteristic optical zone 930 and transition zone 931. Optical zone 930 can have a shape or downward slope that may be linear when plotted against p as shown in FIG. 4A. When plotted against radius r, optical zone 930 can have a shape or downward slope that is parabolic. Central and peripheral echelettes can have a surface area that is between 1 and 7 mm². For example, the echelettes may have a surface area that is 2.3 mm². An outer (refractive) zone can follow the base radius with a fixed offset.

As shown in FIG. 4A, transition zones 931 between the optical zones 930 and the adjacent optical zones can be sharp and discontinuous. Similarly, a vertical transition between adjacent echelettes and also the peripheral portion or refractive zone can be sharp and discontinuous. The height of the lens face sharply transitions from sloping steadily downwards (e.g. across optical zones 930) to stepping vertically upwards (e.g. at transition zone 931), and the transitions abruptly back to sloping steadily downward or substantially horizontal at outer refractive zone. In doing so, echelette 930 also has a characteristic step height 932 defined by the distance between the lowest point and highest point of the echelette. Hence, the slope (or first derivative) and/or curvature (second derivative) of the diffractive surface are discontinuous adjacent the transition. The first derivative can be indicated by the direction of the lines, and the second derivative can be indicated by the curve of the line.

According to some embodiments, light comes from below, in the direction indicated by arrow A, and only hits the echelettes 930 of the profile. According to some embodiments, in theoretical terms light does not hit the vertical connection of the optical zones, and hence the profile can be said to have no transition zone. According to some embodiments, in practice when one attempts to produce such a profile, for instance by lathe cutting, it may be difficult to reproduce the sharp corner (e.g. at where the optical zone connects with the adjacent optical zone) and hence the corner may be rounded to some extent due to the finite chisel radius. Such rounding may have a negligible effect on the optical performance. According to related embodiments, transition zone 931, which can be referred to as the transition from the echelette to the adjacent zone or zones, can be shaped in a specific way, so as to optimize the optical performance, for example to minimize scatter from a sharp transition.

Profile Parameters

The profile design can be characterized in terms of a set of parameters. For example, the limited echelette profile can be described as having a central echelette with a diameter and surface area, an adjacent echelette(s) with the same surface area, and an associated stepheight at each transition resulting in a phase delay. The central echelette may have a diameter within a range from about 1 mm to about 5 mm. For example, the central echelette may have a diameter of about 1.5 mm. Central echelette may have a surface area that is between 1 and 7 mm$^2$. For example, the central echelette may have a surface area that is 2.3 mm$^2$. The peripheral echelette(s) may have a surface area equal to the central echelette. In particular, Table 1 discloses the dimensions of the radius and diameter of the central echelette, along with the surface area of the central and peripheral echelettes.

| R (mm) | De (mm) | Area (mm$^2$) |
| --- | --- | --- |
| 1.48 | 3 | 6.9 |
| 1.05 | 2.1 | 3.5 |
| 0.86 | 1.7 | 2.3 |
| 0.74 | 1.5 | 1.7 |
| 0.66 | 1.3 | 1.4 |
| 0.61 | 1.2 | 1.2 |

The step height or profile height can determine the phase delay or phase shifting profile. A greater step height can correspond to a greater phase shift. According to some embodiments, a lens can include a transition characterized by a step height producing a phase shift between about 0.25 and about 1 times the design wavelength. In some cases, a diffractive profile can be characterized by a design wavelength, and the lens can include a transition characterized by a step height producing a phase shift between about 0.15 and about 2 times the design wavelength. According to some embodiments the lens may include a transition characterized by a step height producing a phase shift of about 0.5. In other embodiments, the lens may include a transition characterized by a step height of about 0.4.

Table 2 provides dimensions of various samples disclosing the relationship between phase delay (in wavelengths) and step height (in μm), as valid for an example IOL material.

TABLE 2

| Phase Delay | Stepheight |
| --- | --- |
| 0.896 | 3.68 |
| 0.700 | 2.87 |
| 0.590 | 2.42 |
| 0.509 | 2.09 |
| 0.500 | 2.05 |
| 0.423 | 1.74 |
| 0.366 | 1.50 |
| 0.350 | 1.44 |
| 0.250 | 1.03 |
| 0.150 | 0.62 |

Figure 4B:
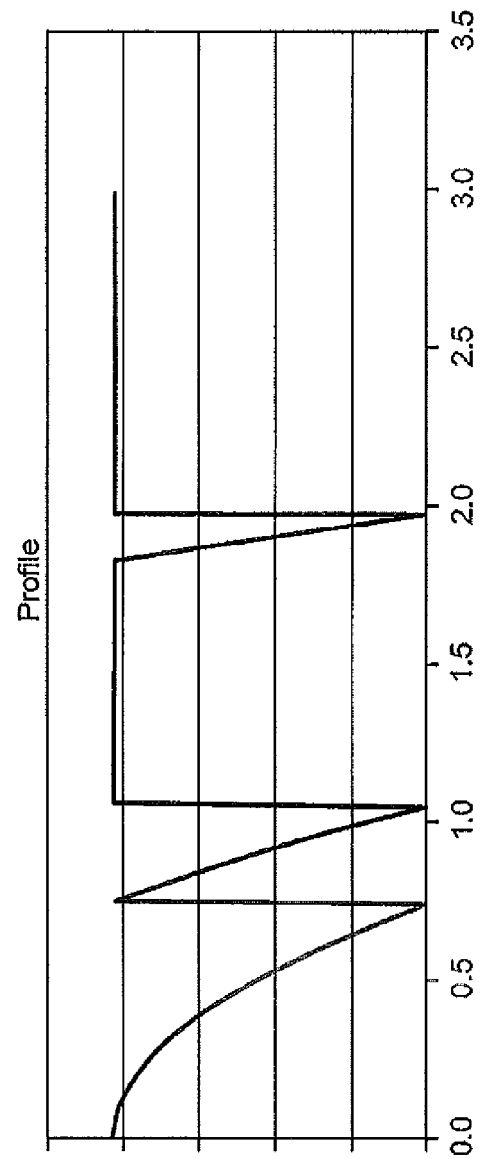

FIG. 4B provides a graphical representation of a portion of a lens diffractive profile with a central echelette and two peripheral echelettes according to embodiments of the present invention. The height of the surface relief profile (from a plane perpendicular to the light rays) of each point on the echelettes surface is plotted against the distance from the optical axis of the lens. According to some embodiments, a lens with a central and peripheral adjacent echelette, as disclosed in FIG. 4A may also be comprised of an additional peripheral echelette with a refractive region between the outermost echelette and the interior echelettes.

Figure 4C:
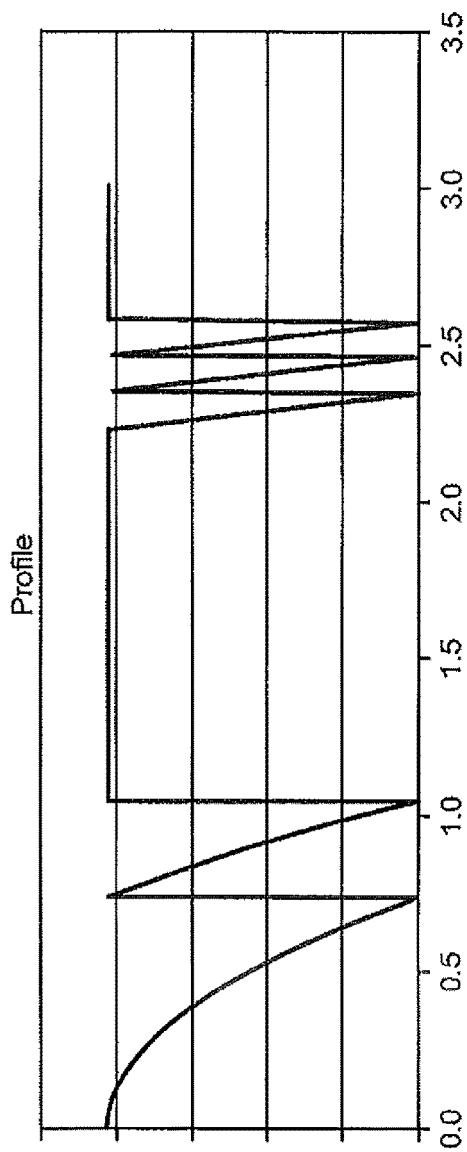

FIG. 4C also details a portion of a lens diffractive profile with a central echelette and two peripheral echelettes. In this embodiment, however, the refractive zone is immediately adjacent to the central echelette and separates the central echelette from three peripheral and adjacent echelettes.

Figure 4D:
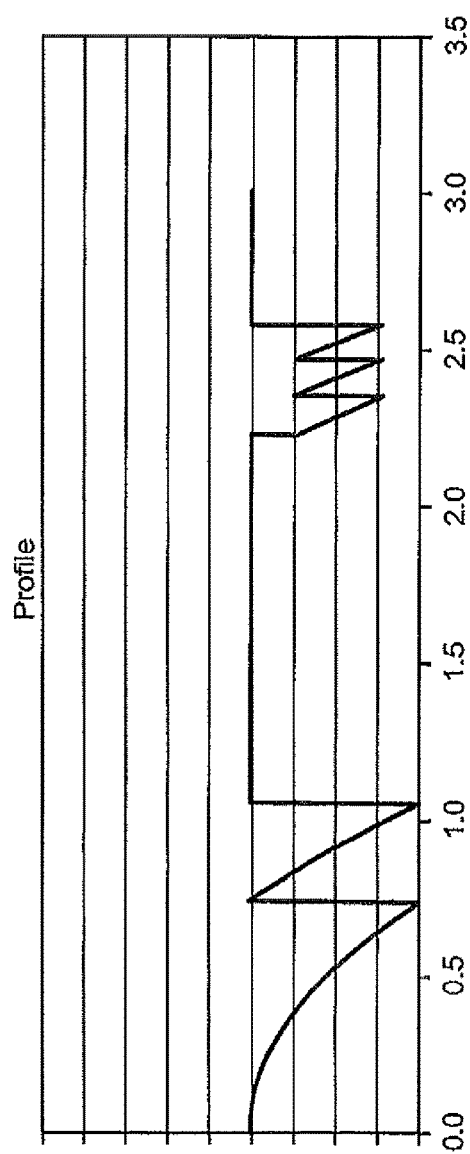

Although the above preferred embodiments disclose lenses with echelettes that have equal stepheights, lenses with echelettes with varying stepheights are also covered herein as detailed in FIG. 4D. FIG. 4D. discloses a four echelette embodiment wherein a refractive region separates the central and adjacent echelette from three peripheral adjacent echelettes. As seen in FIG. 4D, the stepheight (defined by the distance between the lowest point and highest point of the echelette) of the three outer echelettes is less than the stepheight of the inner echelettes. Of course, in addition to covering embodiments where the stepheight of the outer echelette(s) is less than the inner echelette(s), the stepheight of the inner echelette(s) may be less than the outer echelette(s). It is also foreseeable, that the inner and outer echelettes may all have varying stepheights whether the stepheights be increasing, decreasing, or alternating.

Figure 4E:
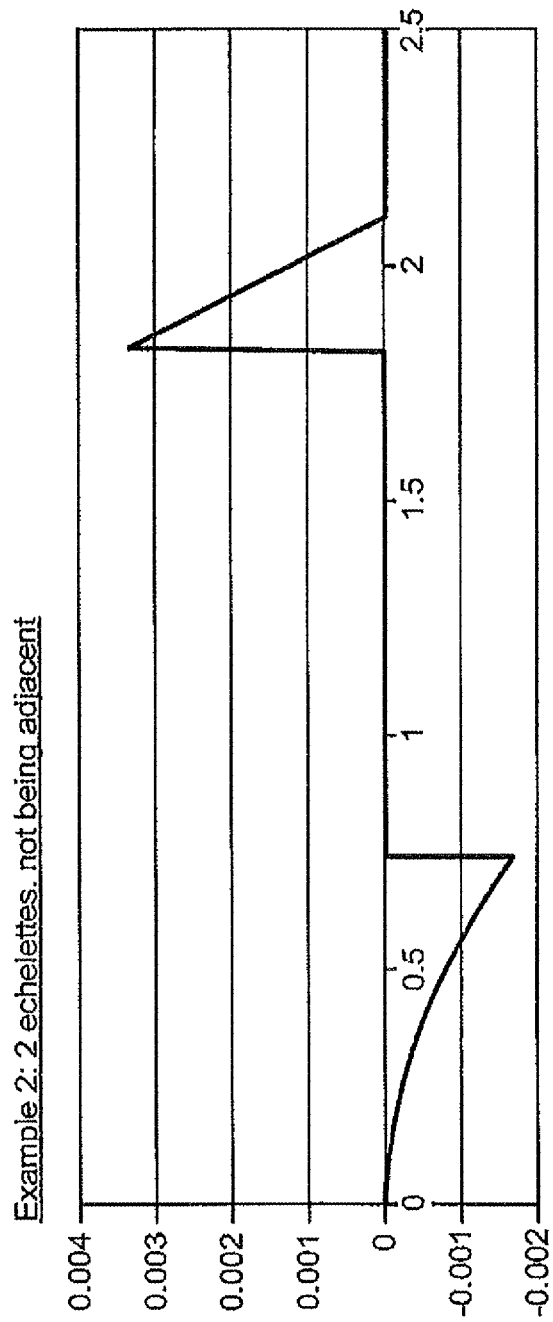

FIG. 4E provides a graphical representation of a portion of a lens diffractive profile with a central echelette and a peripheral echelette which is not adjacent to the central echelette. The central echelette may have a shape or downward slope that is parabolic. A refractive region may then separate the central echelette from the peripheral echelette. The peripheral echelette may then be characterized by a sharp and discontinuous stepheight followed by a downward slope. As in the embodiments above, a peripheral refractive region may surround the outermost echelette. Additionally, other exemplary embodiments include non-adjacent echelette variations analogous to FIG. 4A-4D. By way of non-limiting example, two echelettes that are not separated by a refractive region may also be non-adjacent.

Pupil Dependence

The size of the human pupil varies with illumination. In bright light the pupil is small, and in dim or low light conditions the pupil is large. In addition, the size of the human pupil varies with accommodative effort. Without accommodative effort, the pupil is larger than with accommodative effort. Hence, for a smaller pupil, it may be desirable to provide a design that places a relative emphasis on intermediate or near vision. For a larger pupil, it may be desirable to provide a design that places a relative emphasis on far vision.

In typical reading or near vision conditions where the light is bright, the size of the pupil is small, e.g. between about 1 mm and 2 mm in diameter, and the eye has a large depth of focus (for example from a pinhole effect), almost irrespective of the optics of the IOL. When the size of the pupil is large, e.g. larger than about 4-5 mm in diameter, the situation generally applies to low light conditions, and is often associated with distance vision for which the power of the IOL is typically established. Therefore, many patients would benefit most from an IOL that enhances the depth of focus in order to view at intermediate distances. An IOL having a central echelette with limited adjacent echelettes may effectively increase the depth of focus for intermediate pupil sizes, while maintaining the general increased depth of focus of small pupil sizes, and also maintaining an emphasis on far vision for large pupil sizes.

At the same time, since the limited echelettes and the remaining surface area of the optic or remaining lens portion ("non-echelette") have unequal surface areas for almost all pupil sizes, there is an incomplete split between the foci. The condition of dysphotopsia (e.g. halos) that is present for multifocal lenses is observed to be dominated by separation of two foci and pupil size effects. Accordingly, pursuant to exemplary embodiments of the present invention, the lens may include only a limited number of echelettes, so that light separation between distinct foci is not complete, as compared to standard diffractive multifocal IOLs. Since the split of light is incomplete, the separation of foci is incomplete. The incomplete separation of foci contributes to the extended depth of focus and the attenuation of dysphotopsia (e.g. halos).

In an exemplary embodiment, the limited echelette design has an optical performance that depends on the pupil size. For very small pupils, where the pupil is smaller than the size of the central and adjacent echelette(s), the echelette will act as a refractive lens, having a very large depth of focus due to the pinhole effect. For medium and higher pupil sizes, where the pupil covers the central echelette and the adjacent echelette, the lens will act as a diffractive/refractive lens, directing the light to several foci. For higher pupil sizes, more light is being directed to the lower order foci. The size of the central and adjacent echelette(s) influences the pupil dependence of the lens. As such, the size of the central and adjacent echelette(s) can be chosen, depending on the pupil sizes of a specific patient. For example, the pupil sizes of a patient may be measured in bright light, in dim light, during far vision and during near vision, and in the different combinations of light level and accommodative effort. These different pupil sizes, which may be defined as pupil dynamics, can be used as input parameters for an optimal design of the limited echelette design.

For example, if a patient has a pupil diameter during near vision (e.g. viewing target at close distance, with high accommodative effort) smaller than 2 mm, having this pupil dimension with both bright and dim light, then the size of the central and adjacent echelette(s) may be selected to be smaller than 2 mm (e.g. outer diameter of the adjacent echelette of FIG. 4A), as to provide adequate near and intermediate vision. Relatedly, if a patient has a pupil diameter during near vision larger than 2 mm, having this pupil dimension with both bright and dim light, then the size of the central and adjacent echelette(s) may be 2 mm or larger, as to provide adequate near and intermediate vision. In general, the diameter of the central and adjacent echelette(s) can be smaller than the smallest pupil size the patient has under any condition (e.g. bright/dim light; near/far vision). For any type of pupil dynamics, the size, the profile, and the offsets may be chosen to maximize the lens performance for that specific patient, or group of patients. Generally, this is a trade off between the different vision circumstances (combinations of light level and accommodative effort) at which the pupil of the patient is measured. Accordingly, exemplary embodiments include a method of designing an ophthalmic lens comprised of utilizing pupil size measurements and based on the measurements determining the size of an isolated echelette to impose on the surface of a lens. The pupil size measurements may be based on a group of patients.

Evaluation of Variations of a Specific Example

Figure 5:
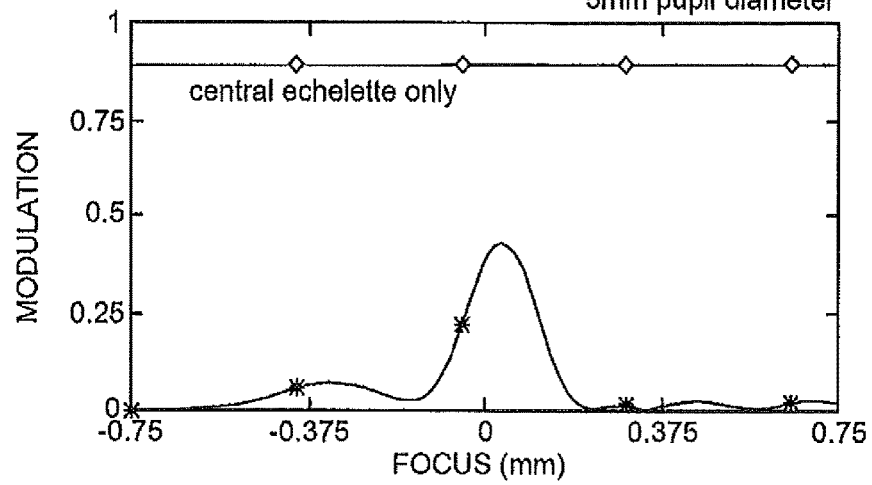
FIG. 5 shows aspects of calculated defocus curves according to a central echelette embodiment.
Figure 6:
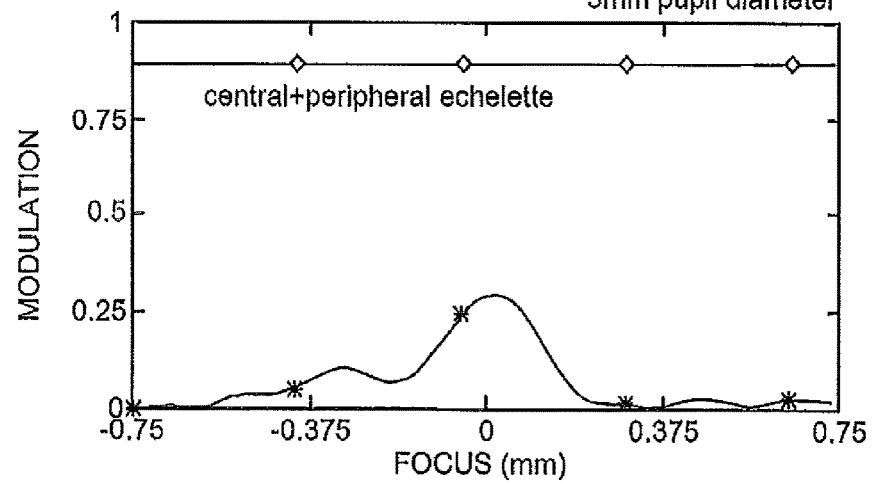
FIG. 6 shows aspects of calculated defocus curves according to a embodiments of the present invention.

FIGS. 5 and 6 show calculated defocus curves in the ACE eye model of an embodiment with a central ring diameter of 1.48 mm, an echelette surface area of 1.7 mm², and a phase delay of 0.4 wavelength. The horizontal axis denotes the defocus value in the image plane, in millimeters. Negative defocus values represent the myopic eye, and therefore, simulate vision at intermediate and near distances. The vertical axis denotes the modulus (MTF) at 50 cycles per millimeter. Data for 5 mm pupil diameters is included. FIG. 5 shows the defocus curve for an embodiment having only a single central echelette. FIG. 6 shows an exemplary embodiment as disclosed in section 4E, having, in addition to the central echelette, a peripheral echelette. The peripheral echelette and has a surface area of 3.5 mm², and a phase delay of 0.82 wavelength. The MTF at intermediate vision distances, with defocus values of about −0.2 mm to −0.3 mm, as shown in FIG. 6 is higher than the MTF at corresponding defocus values in FIG. 5. As illustrated in the figures, a central plus peripheral echelette increases the depth of focus as compared to a central echelette only.

Embodiments of the present invention may be combined with a multifocal lens design, and with that extend the depth of focus of each focus of the multifocal lens. Similarly, embodiments of the present invention may be combined with an accommodating lens design, by which the range of accommodation of the accommodating lens can be extended. In addition, embodiments of the present invention may be combined with lenses correcting ocular aberrations, like toric lenses, aspherical lenses, lenses correcting chromatic aberrations, and the like.

Embodiments of the present invention may be combined with a lens design correcting chromatic aberrations. In one embodiment, the phase delay of the echelettes in the preceding examples is increased by a discrete multiple of wavelengths, in order to correct for chromatic aberration. For example, if a phase delay of 0.5 was used, corresponding to a stepheight of 2.05 μm, an alternative embodiment would have a phase delay of 1.5, corresponding to a stepheight of 6.15 μm. This embodiment directs the first order diffraction to the far focus, and the second order diffraction establishes the depth of focus at the intermediate and near range.

While the exemplary embodiments have been described in some detail, by way of example and for clarity of understanding, those of skill in the art will recognize that a variety of modification, adaptations, and changes may be employed. Hence, the scope of the claims should not be limited to the description of the preferred versions contained herein.

What is claimed is:

1. An ophthalmic lens, comprising:
   an anterior face and a posterior face, the faces disposed about an optical axis; and
   at least one diffractive profile imposed on the anterior face or the posterior face, the at least one diffractive profile consisting of an inner echelette and 1 or 2 peripheral echelettes,
   wherein the inner echelette and the 1 or 2 peripheral echelettes have respective sizes determined by a plural set of measured pupil dynamics;
   wherein the plural set of measured pupil dynamics is measured in a plurality of light levels.

2. The ophthalmic lens of claim 1, wherein at least 2 echelettes are not adjacent to each other.

3. The ophthalmic lens of claim 2, wherein the at least 2 echelettes that are not adjacent to each other are separated by a refractive region.

4. The ophthalmic lens of claim 2, wherein the at least 2 echelettes are not separated by a refractive region.

5. The ophthalmic lens of claim 1, wherein the inner echelette and the peripheral echelette(s) are not separated by a refractive region.

6. The ophthalmic lens of claim 1, wherein the echelettes further comprise of transitions characterized by a step height having a value within a range from about 0.5 μm and about 4 μm.

7. The ophthalmic lens of claim 6, wherein the step height for at least 2 echelettes differ.

8. The ophthalmic lens of claim 6, wherein the surface area for at least 2 echelettes differ.

9. The ophthalmic lens of claim 1, wherein the inner echelette and the peripheral echelettes are characterized by a constant phase shift.

10. The ophthalmic lens of claim 1 further comprising an outer echelette, wherein the inner and outer echelettes have varying step heights.

11. The ophthalmic lens of claim 1, wherein the set of measured pupil dynamics is based on a group of patients.

12. An ophthalmic lens, comprising:
an anterior face and a posterior face, the faces disposed about an optical axis; and
at least one diffractive profile imposed on the anterior face or the posterior face, the at least one diffractive profile consisting of an inner echelette and 1 or 2 peripheral echelettes, wherein the inner echelette and the 1 or 2 peripheral echelettes have respective sizes determined by a plural set of measured pupil dynamics;
wherein the set of measured pupil dynamics is measured in a plurality of accommodative efforts.

13. An ophthalmic lens, comprising:
an anterior face and a posterior face, the faces disposed about an optical axis; and
at least one diffractive profile imposed on the anterior face or the posterior face, the at least one diffractive profile consisting of an inner echelette and 1 or 2 peripheral echelettes, wherein the inner echelette and the 1 or 2 peripheral echelettes have respective sizes has a size determined by a plural set of measured pupil dynamics;
wherein the set of measured pupil dynamics is measured in bright light, in dim light, during far vision, during near vision, and in a plurality of different combinations of the light levels and the accommodative efforts.

14. The ophthalmic lens of claim 12, wherein at least 2 echelettes are not adjacent to each other.

15. The ophthalmic lens of claim 14, wherein the at least 2 echelettes that are not adjacent to each other are separated by a refractive region.

16. The ophthalmic lens of claim 14, wherein the at least 2 echelettes are not separated by a refractive region.

17. The ophthalmic lens of claim 12, wherein the inner echelette and the peripheral echelette(s) are not separated by a refractive region.

18. The ophthalmic lens of claim 12, wherein the echelettes further comprise of transitions characterized by a step height having a value within a range from about 0.5 μm and about 4 μm.

19. The ophthalmic lens of claim 18, wherein the step height for at least 2 echelettes differ.

20. The ophthalmic lens of claim 18, wherein the surface area for at least 2 echelettes differ.

21. The ophthalmic lens of claim 12, wherein the inner echelette and the peripheral echelettes are characterized by a constant phase shift.

22. The ophthalmic lens of claim 12 further comprising an outer echelette, wherein the inner and outer echelettes have varying step heights.

23. The ophthalmic lens of claim 12, wherein the set of measured pupil dynamics is based on a group of patients.

24. The ophthalmic lens of claim 13, wherein at least 2 echelettes are not adjacent to each other.

25. The ophthalmic lens of claim 24, wherein the at least 2 echelettes that are not adjacent to each other are separated by a refractive region.

26. The ophthalmic lens of claim 24, wherein the at least 2 echelettes are not separated by a refractive region.

27. The ophthalmic lens of claim 13, wherein the inner echelette and the peripheral echelette(s) are not separated by a refractive region.

28. The ophthalmic lens of claim 13, wherein the echelettes further comprise of transitions characterized by a step height having a value within a range from about 0.5 μm and about 4 μm.

29. The ophthalmic lens of claim 28, wherein the step height for at least 2 echelettes differ.

30. The ophthalmic lens of claim 28, wherein the surface area for at least 2 echelettes differ.

31. The ophthalmic lens of claim 13, wherein the inner echelette and the peripheral echelettes are characterized by a constant phase shift.

32. The ophthalmic lens of claim 13 further comprising an outer echelette, wherein the inner and outer echelettes have varying step heights.

33. The ophthalmic lens of claim 13, wherein the set of measured pupil dynamics is based on a group of patients.

* * * * *